(12) United States Patent
Yoshida et al.

(10) Patent No.: US 12,048,577 B2
(45) Date of Patent: Jul. 30, 2024

(54) X-RAY FLUOROSCOPIC IMAGING APPARATUS AND X-RAY FLUOROSCOPY IMAGING PROCESS

(71) Applicant: SHIMADZU CORPORATION, Kyoto (JP)

(72) Inventors: Koki Yoshida, Kyoto (JP); Fumiaki Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 95 days.

(21) Appl. No.: 17/548,855

(22) Filed: Dec. 13, 2021

(65) Prior Publication Data

US 2022/0218299 A1    Jul. 14, 2022

(30) Foreign Application Priority Data

Jan. 14, 2021 (JP) .................. 2021-004449

(51) Int. Cl.
*A61B 6/00* (2024.01)
*A61B 6/04* (2006.01)

(52) U.S. Cl.
CPC ............ *A61B 6/547* (2013.01); *A61B 6/0407* (2013.01); *A61B 6/4441* (2013.01); *A61B 6/4476* (2013.01); *A61B 6/487* (2013.01)

(58) Field of Classification Search
CPC .......... A61B 6/487; A61B 6/54; A61B 6/4476
See application file for complete search history.

(56) References Cited

U.S. PATENT DOCUMENTS 6,334,708 B1 * 1/2002 Kosugi .................. A61B 6/504
378/68

FOREIGN PATENT DOCUMENTS

| JP | 2000-197621 A | 7/2000 |
| JP | 2006-109891 A | 4/2006 |
| JP | 2008-125981 A | 6/2008 |

OTHER PUBLICATIONS

Notice of Reasons for Refusal with the drafting date of Nov. 28, 2023 (together with a machine translation thereof) for corresponding Japanese Patent Application No. 2021-004449.

* cited by examiner

*Primary Examiner* — Dani Fox
(74) *Attorney, Agent, or Firm* — Muir Patent Law, PLLC

(57) ABSTRACT

In this X-ray fluoroscopic imaging apparatus, a control unit includes a first determination unit for determining whether or not X-ray imaging has been performed and is configured to perform control to switch to the target position to the next target position when it is determined by a first determination unit that X-ray imaging has been performed.

7 Claims, 9 Drawing Sheets

FIG. 2A
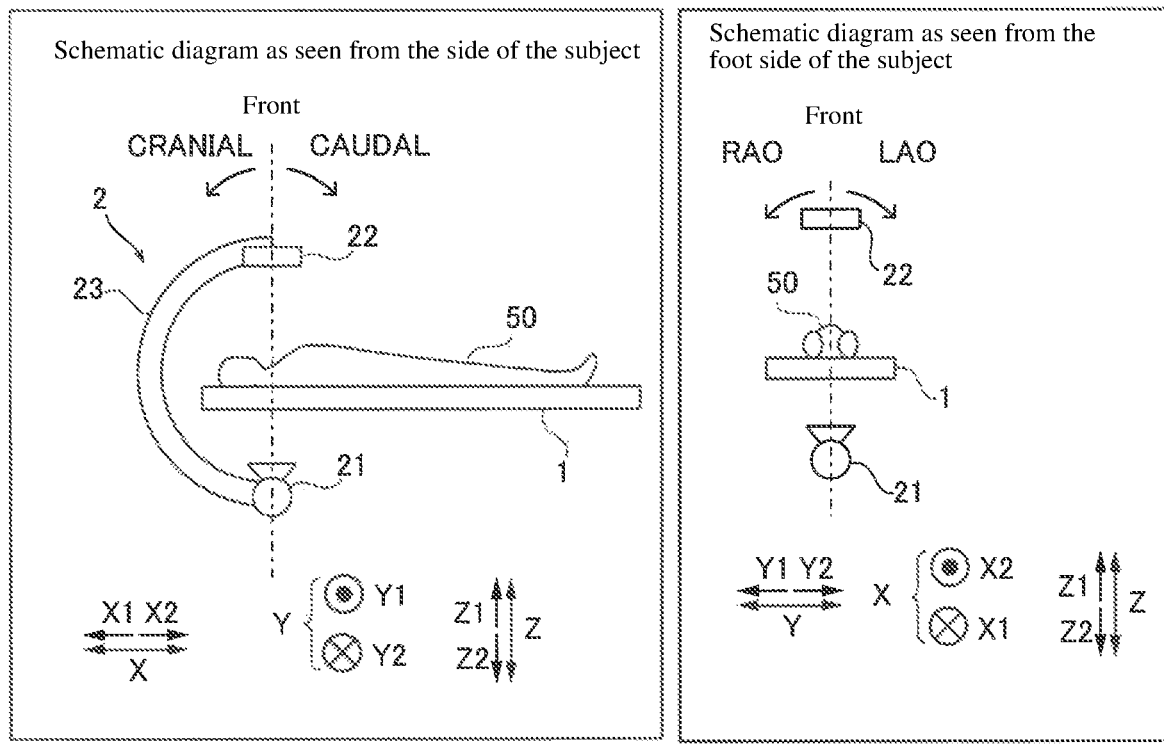
FIG. 2B
FIG. 3
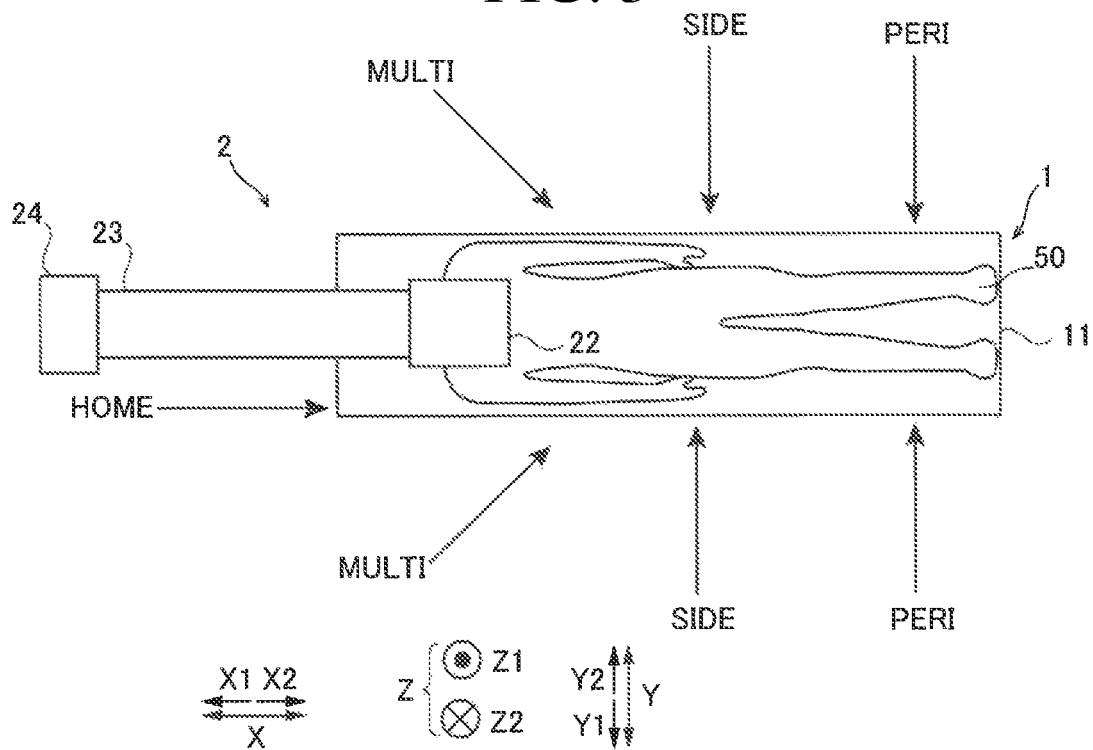

Second modification

X-RAY FLUOROSCOPIC IMAGING APPARATUS AND X-RAY FLUOROSCOPY IMAGING PROCESS

CROSS-REFERENCE TO RELATED APPLICATIONS

The related application No. JP2021-004449, entitled "X-Ray Fluoroscopic Imaging Apparatus and X-Ray Fluoroscopy Imaging Method," filed on Jan. 14, 2021, invented by Koki YOSHIDA, and Fumiaki TANAKA, upon which this patent application is based is hereby incorporated by reference in its entirety.

BACKGROUND OF THE INVENTION

Field of the Invention

The present invention relates to an X-ray fluoroscopic imaging apparatus and an X-ray fluoroscopic imaging method. In particular, the present invention relates to an X-ray fluoroscopic imaging apparatus equipped with a storage unit for storing a plurality of target positions serving as targets toward which an imaging unit is moved and the order of moving the imaging unit toward the plurality of target positions in an associated manner, and also related to an X-ray fluoroscopic imaging method.

Description of the Background Art

Conventionally, an X-ray fluoroscopic imaging apparatus equipped with a storage unit for storing a plurality of target positions serving as targets toward which the imaging unit is moved and the order of moving the imaging unit toward the plurality of target positions in an associated manner is known. Such an apparatus is disclosed in, for example, Japanese Unexamined Patent Application Publication No. 2000-197621.

The medical imaging apparatus described in Japanese Unexamined Patent Application Publication No. 2000-197621 is provided with: an imaging means for imaging a medical image relating to a subject; a support mechanism for supporting the imaging means at various positions; a means for storing a plurality of positions of the imaging means and the order as data in an associated manner; and a control means for controlling the support mechanism in accordance with the stored positions and the order to sequentially change the position of the imaging means.

In the medical imaging apparatus disclosed in Japanese Unexamined Patent Application Publication No. 2000-197621, the control means is configured to move the imaging means to stored positions in accordance with sequential positioning data composed of data of the positions of the imaging means stored in the storing means and the order. When the next positioning switch is pressed after completion of the imaging, the control unit reads out the data relating to the next position from the storing means and moves the imaging unit to the next position.

Here, although not described in the above-described Japanese Unexamined Patent Application Publication No. 2000-197621, imaging is sometimes performed by finely adjusting the imaging position because there is an individual difference depending on a subject. Further, in some cases, imaging is performed at a position not stored during a series of imaging at each imaging position.

However, in the X-ray fluoroscopic imaging apparatus configured to read out the data of the next imaging position when the imaging unit has moved to the position stored in the storage unit, there are the following issues. That is, in a case where imaging has been performed by stopping the imaging unit between the current position and the next position, or in a case where imaging has been performed at a position not stored, there are the following problems. That is, the next imaging position will not be read because the movement of the imaging unit has not yet been completed. Further, since the next imaging position is not read, the next imaging position (target position) must be selected again, and then the positioning switch must be pressed again.

SUMMARY OF THE INVENTION

The present invention has been made to solve the above-described problems. It is an object of the present invention to provide an X-ray fluoroscopic imaging apparatus capable of switching the imaging position to the next target position without selecting the next target position when imaging has been performed at any imaging position.

In order to attain the above-described objects, an X-ray fluoroscopic imaging apparatus according to one aspect of the present invention includes: a bed configured to place a subject thereon; an imaging unit including an X-ray source for irradiating the subject with X-rays, a detector for detecting X-rays emitted from the X-ray source, the detector facing the X-ray source, and an arm for connecting the X-ray source and the detector; a storage unit configured to store a plurality of target positions serving as targets toward which the imaging unit is moved and an order of moving the imaging unit to the plurality of target positions in an associated manner; a control unit configured to sequentially switch the plurality of target positions according to the order; and a drive unit configured to move the imaging unit toward a target position switched by the control unit. The control unit includes a first determination unit configured to determine whether or not X-ray imaging has been performed. When it is determined by the first determination unit that X-ray imaging has been performed, the control unit is configured to perform control to switch the target position to a next target position.

In the X-ray fluoroscopic imaging apparatus according to the above-described one aspect of the present invention, the control unit includes a first determination unit for determining whether or not X-ray imaging has been performed and is configured to perform control to switch the imaging position to the next target position when it is determined by the first determination unit that X-ray imaging has been performed. Thus, when it is determined by the first determination unit that X-ray imaging has been performed, the control unit performs control to switch the imaging position to the next target position. With this, when the imaging is completed regardless of the position of the imaging unit after moving, the control unit performs control to switch the target position. For this reason, the target position can be switched even in a case where imaging has been performed at a position other than the target position. Consequently, when imaging has been performed at any imaging position, the imaging position can be switched to the next target position without selecting the next imaging position.

BRIEF DESCRIPTION OF THE DRAWINGS

FIG. 2A is a schematic diagram for explaining imaging directions as viewed from the side of the subject.

FIG. 2B is a schematic diagram for explaining imaging directions as viewed from the foot side of the subject.

FIG. 3 is a diagram for explaining relative positions between a bed and an imaging unit.

DESCRIPTION OF THE PREFERRED EMBODIMENT

Hereinafter, an embodiment in which the present invention is embodied will be described with reference to the attached drawings.

Overall Configuration of X-Ray Fluoroscopic Imaging Apparatus

Referring to FIG. 1 to FIG. 8, an X-ray fluoroscopic imaging apparatus 100 according to an embodiment of the present invention will be described.

Figure 1:
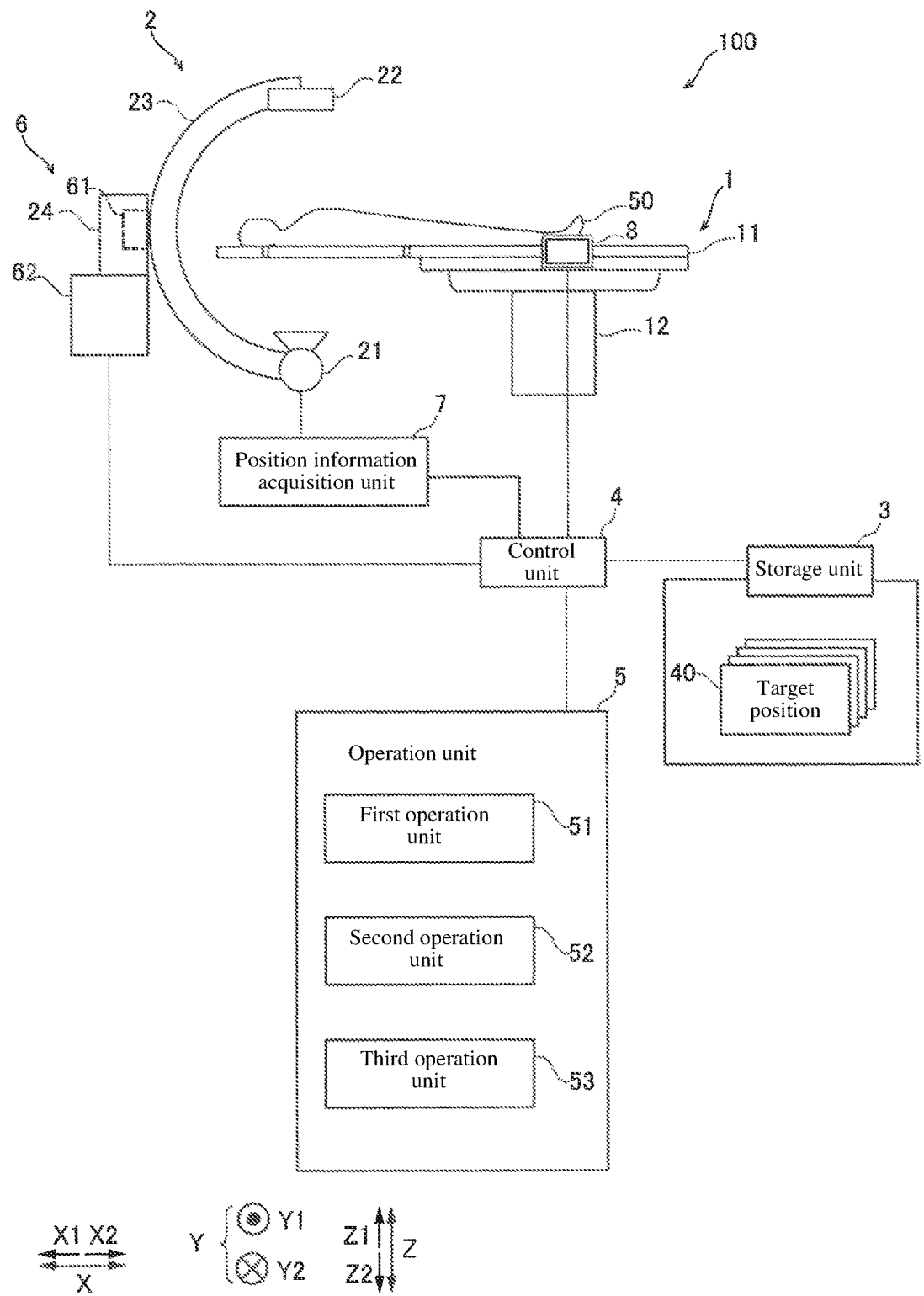
FIG. 1 is a diagram for explaining the configuration of an X-ray fluoroscopic imaging apparatus.

As shown in FIG. 1, the X-ray fluoroscopic imaging apparatus 100 is a device for diagnosing a disease in a target site of a subject 50. The target site is, for example, a blood vessel (coronary artery) of a heart but may also be an abdomen or a lower limb.

The X-ray fluoroscopic imaging apparatus 100 according to this embodiment is provided with a bed 1, an imaging unit 2, a storage unit 3, a control unit 4, an operation unit 5, a drive unit 6, and a position information acquisition unit 7. The X-ray fluoroscopic imaging apparatus 100 sequentially images the target sites at a plurality of angles and positions based on a plurality of target positions 40 stored in the storage unit 3.

Note that, in this embodiment, the mode in which the X-ray fluoroscopic imaging apparatus 100 sequentially images the target sites based on the plurality of target positions 40 stored in the storage unit 3 at the plurality of angles and positions will be referred to as a sequence mode.

The bed 1 includes a top board 11 configured to place a subject 50 thereon and a base 12 configured to support the bed 1 from below. The subject 50 is laid on the top board 11 such that the longitudinal direction of the bed 1 (top board 11) and the head-to-foot direction of the subject 50 coincide. Here, in the state shown in FIG. 1, the longitudinal direction of the bed 1 is defined as an X-direction. Further, the side on which the head of the subject 50 is placed is defined as an X1 side, and the side on which the foot is placed is defined as an X2 side. The short direction (left-right direction of the subject 50) of the bed 1 perpendicular to the X-direction is defined as a Y-direction. The right hand side of the subject 50 when the subject 50 lies on the back is defined as a Y1 side, and the left hand side is defined as a Y2 side. Further, the up-down direction of the bed 1 orthogonal to the X-direction and the Y-direction is defined as a Z-direction. Further, the top board 11 side is defined as a Z1 side, and the base 12 side is defined as a Z2 side. The base 12 is provided at a part of the bottom surface side (Z2 side) of the bed 1.

The imaging unit 2 is provided with an X-ray source 21, a detector 22, and an arm 23. The X-ray source 21 includes an X-ray tube (not shown). The X-ray tube is configured to heat an anode and a cathode therein by passing a current therethrough and emit X-rays when the thermal electrons ejected from the cathode by applying a voltage between the anode and the cathode collide against the anode. Further, it is configured such that the X-rays generated by the X-ray tube are emitted toward the detector 22. When the tube voltage applied to the X-ray tube is changed, the X-ray fluoroscopic dose (irradiation intensity) of the X-rays to be emitted is determined according to the tube voltage. Further, the X-ray source 21 is configured to transmit a signal to the control unit 4 while emitting X-rays.

The detector 22 is, for example, an FPD (Flat Panel Detector). The detector 22 is configured to receive the X-rays emitted from the X-ray source 21 and transmitted through the subject 50, and converts the received X-rays into an electric signal. The detector 22 has an imaging element (not shown) having a plurality of pixels (zones) therein, detects the intensity of the X-rays for each corresponding pixel, and converts the X-ray information (detection signal) for each pixel into an electric signal (digital data) as a pixel value. The X-ray information converted into an electric signal is transmitted to the control unit 4.

The arm 23 has an arcuate shape. The X-ray source 21 is connected to one end of the arm 23, and the detector 22 is connected to the other end of the arm 23. The arm 23 is a so-called C-shaped arm. By means of the arm 23, the X-ray source 21 and the detector 22 are arranged so as to face each other across the subject 50 lying on the bed 1. The base 12 of the bed 1 is provided only at a part of the top board 11. Therefore, it is possible to insert the arm 23 at the portion not provided with the base 12 to thereby place the X-ray source 21 on the bottom surface side of the bed 1 (Z2 side). In this embodiment, the X-ray fluoroscopic imaging apparatus 100 is a single-plane type equipped with a single arm 23.

The arm 23 is rotatably mounted on the arm base 24. The arm base 24 is provided with a rotation mechanism 61 for rotating the arm 23 therein. Note that the rotation mechanism 61 is an example of the "drive unit" recited in claims.

The imaging unit 2 is configured to perform imaging from the following directions. That is, the imaging unit 2 is configured to perform imaging from any direction in which a direction along which X-rays are emitted obliquely with respect to the subject 50 from one end side (CRANIAL side) or the other end side (CAUDAL side) in a longitudinal cross-section along the longitudinal direction (X-direction) of the bed 1 for placing the subject 50 thereon as shown in FIG. 2A, the RAO (right anterior oblique) direction, the front direction, and the LAO (left anterior oblique) direction of the subject 50 are combined. Note that the illustration of the arm 23 is omitted in FIG. 2B.

As shown in FIG. 3, the relative position of the imaging unit 2 with respect to the bed 1 differs depending on the site to be imaged. In FIG. 3, the direction of the arrow indicates the direction of inserting the imaging unit 2 between the top board 11 of the bed 1 and the floor. The detector 22 is positioned on the tip end side of the arrow, which is the subject 50 side, and the arm base 24 is positioned on the base end side of the arrow opposite to the tip end side. The position in which the arm 23 is positioned along the longitudinal direction (X-direction) of the bed 1 on the top view is referred to as a "HOME position." The position in which the arm 23 is arranged obliquely from the head side (X1 side) toward the foot side (X2 side) of the subject 50 and from the peripheral portion of the bed 1 in the longitudinal direction (X-direction) toward the subject 50 is referred to as a "MULTI position." The position in which the arm 23 is arranged along the short direction (Y-direction) of the bed 1 from the side of the subject 50 toward the center thereof in the top view is referred to as a "SIDE position." In addition, the position moved from the SIDE position to the foot side (X2 side) of the subject 50 is referred to as a "PERI position." For example, in the case of imaging from the head to the chest of the subject 50, the arm 23 is set to the HOME position. In the case of imaging the lower limb, the arm 23 is set to the PERI position. Further, in the case of imaging the abdomen of the subject 50, the arm 23 is set to the MULTI position or the SIDE position.

As shown in FIG. 1, the storage unit 3 stores a plurality of target positions 40 toward which the imaging unit 2 is moved and the order of moving the imaging unit toward the plurality of target positions 40 in an associated manner. The storage unit 3 is, for example, an HDD (Hard Disk Drive) or a nonvolatile memory.

The control unit 4 controls the imaging unit 2 to image the subject 50 based on the operation via the operation unit 5. Further, the control unit 4 performs control to make the storage unit 3 store target positions 40. Further, the control unit 4 performs control to make the display unit 8 display an image. The control unit 4 is, for example, a CPU (Central Processing Unit).

Figure 4:
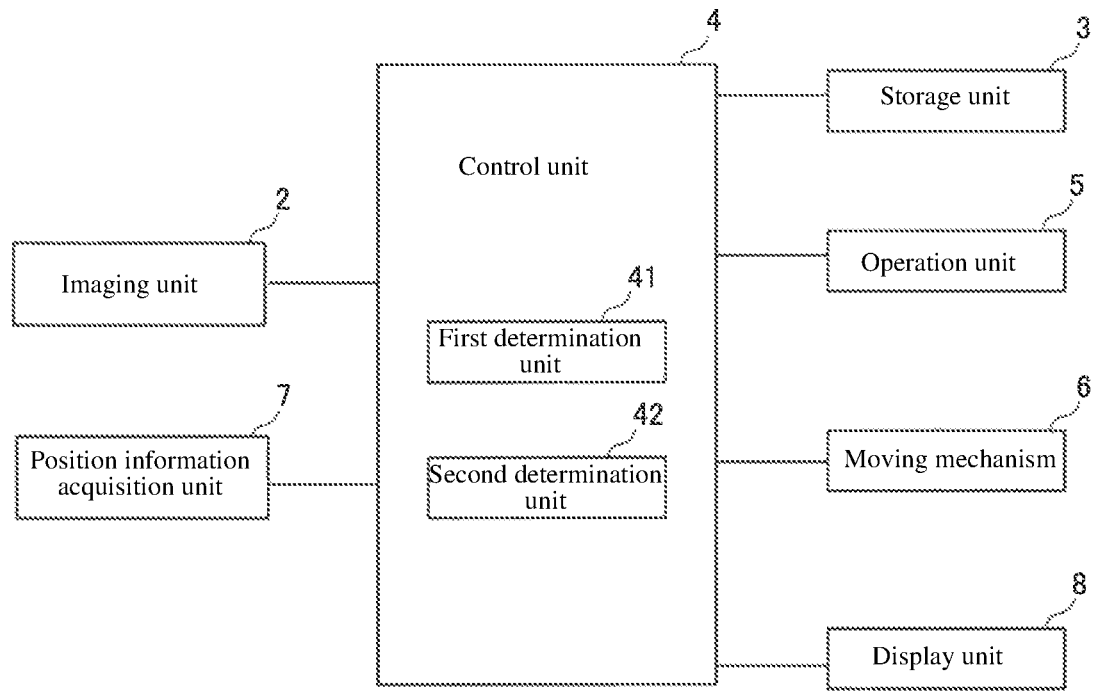
FIG. 4 is a block diagram showing the configuration of the control unit of the X-ray imaging apparatus.

As shown in FIG. 4, the control unit 4 composed of a CPU or the like as hardware includes a first determination unit 41 and a second determination unit 42 as functional blocks of the software. The first determination unit 41 determines whether or not X-ray imaging has been performed. The second determination unit 42 determines whether or not the current position information on the imaging unit 2 acquired by the position information acquisition unit 7 matches the currently selected target position 40. The control unit 4 performs control to sequentially switch a plurality of target positions 40. Further, the control unit 4 performs control to sequentially move the imaging unit 2 toward the plurality of target positions 40 stored in the storage unit 3 based on the operation of moving the imaging unit 2. Specifically, the control unit 4 moves (rotates) the imaging unit 2 by controlling the rotation mechanism 61 (see FIG. 1) to rotate the arm 23.

The first determination unit 41 determines whether or not X-ray imaging has been performed. Specifically, the first determination unit 41 determines whether or not X-ray imaging has been performed based on the signal transmitted from the X-ray source 21 to the control unit 4 during the X-ray irradiation.

The second determination unit 42 determines whether or not the current position information on the imaging unit 2 matches the currently selected target position 40. Specifically, the second determination unit 42 compares the current absolute position of the imaging unit 2 acquired by the position information acquisition unit 7 with the absolute position of the imaging unit 2 at the target position 40. The absolute position is determined, for example, by the position coordinate.

In a case where the second determination unit 42 has determined that the current position information on the imaging unit 2 does not match the currently selected target position 40, i.e., even in a case where the imaging unit 2 after moving has not reached the target position 40, it is determined by the first determination unit 41 that imaging has been completed and the imaging has been performed. With this, the control unit 4 performs control to sequentially switch the plurality of target positions 40. Further, the control unit 4 performs control to switch the target positions 40 upon receipt of the imaging operation via the operation unit 5. Further, when the imaging unit 2 has been moved manually, the control unit 4 performs control to terminate the sequence mode. Note that, when the sequence mode has been terminated, the control unit 4 performs control to set the selected target position 40 to a new target position 40 upon receipt of the operation of selecting a target position 40.

As shown in FIG. 1, the operation unit 5 includes a first operation unit 51, a second operation unit 52, and a third operation unit 53. The first operation unit 51 receives an operation of moving the imaging unit 2 toward the target position 40. The second operation unit 52 receives an operation of moving the imaging unit 2 in a direction different from a direction toward the target position 40. The third operation unit 53 receives an imaging operation. The operation unit 5 is arranged on the side (Y-direction side) of the bed 1.

When the first operation unit 51 is operated, the control unit 4 controls the rotation mechanism 61 and the moving mechanism 62 to rotate or move the arm 23 to thereby move the imaging unit 2 toward the target position 40. Further, when the operation of the first operation unit 51 has been terminated, even if the imaging unit 2 has not yet reached the target position 40, the control unit 4 terminates the control to move the imaging unit 2 toward the target position 40. Furthermore, in a case where the imaging unit 2 has not yet reached the target position 40 and the first operation unit 51 is again operated after the stop of the movement of the imaging unit 2 toward the target position 40, the control unit 4 controls as follows. That is, the control unit 4 controls the rotation mechanism 61 and the moving mechanism 62 to rotate or move the arm 23 to thereby move the imaging unit 2 toward the target position 40. The first operation unit 51 is, for example, a push button. Note that the moving mechanism 62 is an example of the "drive unit" recited in claims.

When the second operation unit 52 is operated, the control unit 4 controls the rotation mechanism 61 and the moving mechanism 62 to rotate or move the arm 23 to thereby move the imaging unit 2 in a direction different from a direction toward the target position 40. The second operation unit 52 is, for example, a lever switch. In this case, the control unit 4 controls the rotation mechanism 61 and the moving mechanism 62 to rotate or move the arm 23 toward the inclination direction of the lever switch.

When the third operation unit 53 is operated, the control unit 4 controls the imaging unit 2 to image the subject 50. The third operation unit 53 is, for example, a foot switch or a hand switch.

The first operation unit 51, the second operation unit 52, and the third operation unit 53 may be provided on one console or may be arranged independently. For example, in a case where the third operation unit 53 is configured by a foot switch, the first operation unit 51 and the second operation unit 52 may be provided on a single console. In a case where the third operation unit 53 is configured by a hand switch, the first operation unit 51, the second operation unit 52, and the third operation unit 53 may be provided on a single console.

Figure 5:
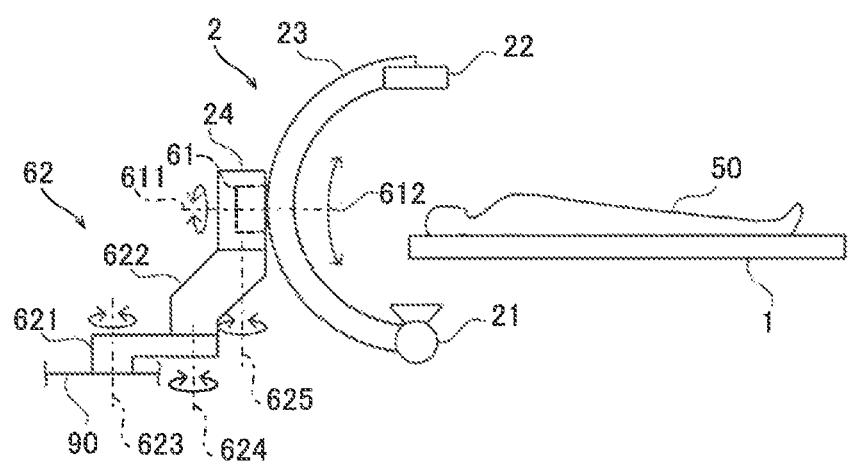
FIG. 5 is a diagram for explaining the configurations of a rotation mechanism and a moving mechanism of the imaging unit.
Figure 5:
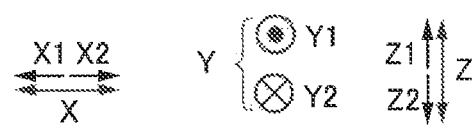

As shown in FIG. 1, the drive unit 6 includes a rotation mechanism 61 and a moving mechanism 62. As shown in FIG. 5, the rotation mechanism 61 rotates the arm 23 about the axis of a rotating shaft 611, which is a line extending in the longitudinal direction (X-direction) of the bed 1 connecting the head and the foot of the subject 50. Further, the rotation mechanism 61 is configured to rotate the arm 23 in the circumferential direction 612 of the arm 23. In this embodiment, the angle at which the arm 23 rotates about the axis of the rotating axis 611 is referred to as a first rotation angle 25 (see FIG. 7A and FIG. 7B). Further, the angle at which the arm 23 is rotated in the circumferential direction 612 of the arm 23 is referred to as a second rotation angle 26 (see FIG. 8A and FIG. 8B). The rotation mechanism 61 includes, for example, a motor and the like.

The moving mechanism 62 is attached to the arm base 24. With the moving mechanism 62, it is possible to move the arm 23 horizontally by moving the arm base 24. The moving mechanism 62 includes a first rotation unit 621 provided on a floor 90 and a second rotation unit 622 rotatably held by the first rotation unit 621 to rotatably hold the arm base 24. The first rotation unit 621 includes a base axis 623 and an intermediate axis 624 provided at a position away from the base axis 623. The second rotation unit 622 includes a horizontal rotation axis 625.

The base axis 623 and the intermediate axis 624 are each a rotation axis oriented in the vertical direction with respect to the floor 90. Further, the horizontal rotation axis 625 is a rotation axis oriented in the vertical direction with respect to the floor 90. This allows the moving mechanism 62 to combine the rotation about the base axis 623, the rotation about the intermediate axis 624, and the rotation about the horizontal rotation axis 625 to move the arm base 24 and the arm 23 horizontally to a desired position.

The position information acquisition unit 7 acquires the current position of the imaging unit 2. Specifically, the position information acquisition unit 7 acquires the absolute position of the imaging unit 2 and the absolute position of the top board 11.

Figure 6:
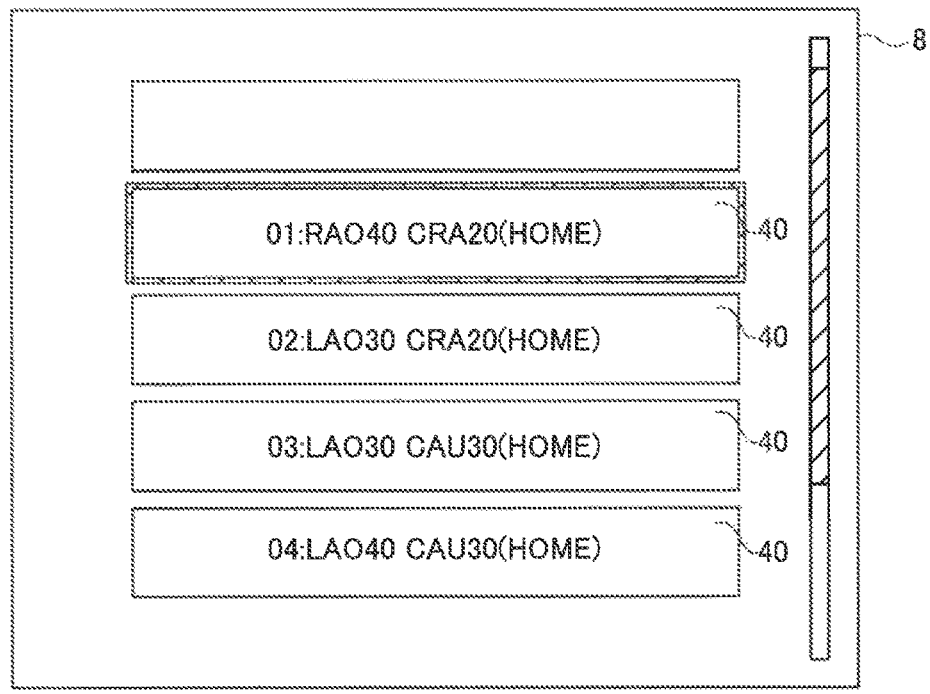
FIG. 6 shows an example of target positions displayed on a display unit.

As shown in FIG. 1, the X-ray fluoroscopic imaging apparatus 100 of this embodiment further includes a display unit 8. The display unit 8 is provided on the side (Y-direction side) of the bed 1. The display unit 8 displays a plurality of target positions 40. The display unit 8 is a touch panel liquid crystal monitor for receiving the operator's operation. The control unit 4 performs control to make the display unit 8 display the current target position 40 in a manner different from the other target positions 40. In this case, the control unit 4 controls, for example, to distinguish the color from the colors of the other target positions 40 with the current target position 40 surrounded by a frame. Alternatively, the control unit 4 performs control to blink the current target position 40. In FIG. 6, an example is shown in which the current target position 40 is surrounded by a hatched frame.

When one of the target positions 40 on the display unit 8 is selected, the target position 40 is switched to the selected target position 40. Therefore, it becomes possible to perform imaging by skipping the imaging of unnecessary target positions 40. Further, by selecting the same target position 40, imaging at the same position can be repeated. The control unit 4 perform control to make the display unit 8 display a plurality of target positions 40 in a list format. Further, the control unit 4 performs control to display a plurality of target positions 40 on the display unit 8 in order. For example, the control unit 4 performs control to make the display unit 8 display a plurality of target positions 40 in the sequential order from the top.

The target position 40 is a position where one target site of a subject 50 registered in advance is imaged at a plurality of angles. The target position 40 includes a rotation angle of the arm 23, a relative position of the arm 23 with respect to the top board 11 of the bed 1, and the distance between the focal position of the X-ray source 21 and the detector 22.

As shown in FIG. 2, the rotation angle of the arm 23 is a combination of an angle for rotating the arm 23 by the rotation mechanism 61 when imaging is performed at either the RAO position or the LAO position and an angle for rotating the arm 23 when imaging is performed either at the CRANIAL position or the CAUDAL position.

As shown in FIG. 6, a plurality of target positions 40 is displayed on the display unit 8. The numerals "01," "02," "03," and "04" among the target positions 40 each show the order of moving the imaging unit 2 toward the target positions 40. Also, "RAO" and "LAO" indicate that imaging is performed at the "RAO" position and at the "LAO" position, respectively. Also, the number after "RAO" or "LAO" indicates the first rotation angle 25 (see FIG. 7A and FIG. 7B). Further, "CRA" and "CAU" indicate that imaging is performed at the CRANIAL position and at the CAUDAL position, respectively. The numbers after "CRA" and "CAU" indicate the second rotation angle 26 (see FIG. 8A and FIG. 8B). "HOME" indicates that the relative position of the imaging unit 2 with respect to the bed 1 is a HOME position (see FIG. 2). The "01:RAO40, CRA20(HOME)" displayed on the display unit 8 indicates that "the first target position 40 is that the arm 23 is rotated at the RAO position of a rotation angle of 40 degrees and at the CRANIAL position of the rotation angle of 20 degrees, and the relative position of the imaging unit 2 with respect to the bed 1 is a HOME position."

Note that the number of target positions 40 is two or more. In FIG. 6, four positions 40, i.e., the first to fourth four target positions 40, are displayed, but the fifth and subsequent target positions 40 can be displayed by scrolling.

Figure 7A:
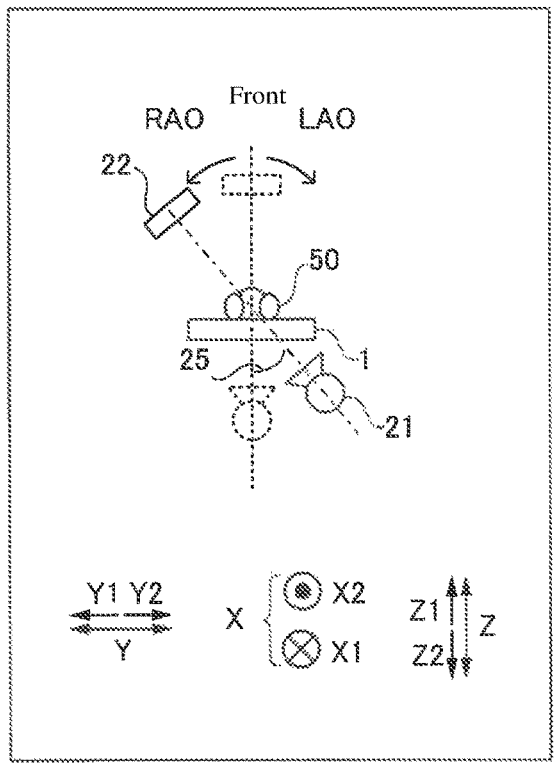
FIG. 7A is a diagram for explaining the rotation of an arm about a rotating axis by a rotation mechanism when imaging at an RAO position.
Figure 7B:
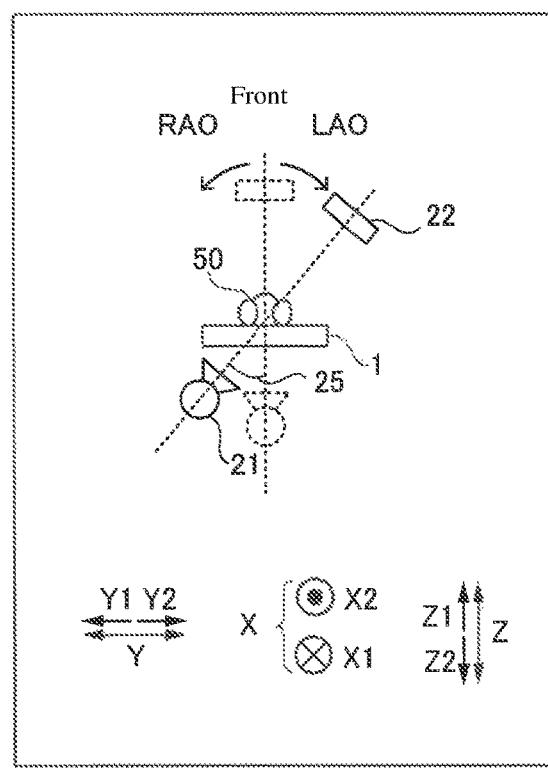
FIG. 7B is a diagram for explaining the rotation of an arm about a rotating axis by a rotation mechanism when imaging at an LAO position.

As shown in FIG. 7A, in a case where the target position 40 (see FIG. 1) is a RAO position, the control unit 4 controls the rotation mechanism 61 so as to rotate the arm 23 in the Y1-direction from the position shown by the dotted line to the position shown by the solid line. Further, as shown in FIG. 7B, in a case where the target position 40 is a LAO position, unlike the case of the RAO position, the control unit 4 controls the rotation mechanism 61 so as to rotate the arm 23 in the Y2-direction from the position shown by the dotted line to the position shown by the solid line. Note that the position shown by the dotted line is a position where the arm 23 is to be placed first and a combination of the front positions in FIG. 2A and FIG. 2B.

Figure 8A:
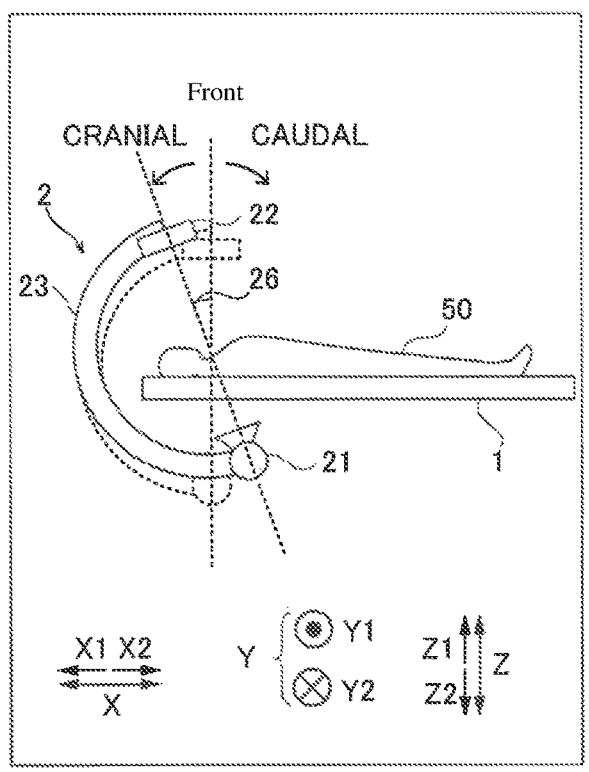
FIG. 8A is a diagram for explaining a circumferential rotation of an arm by a rotation mechanism when imaging at a CRANIAL position.
Figure 8B:
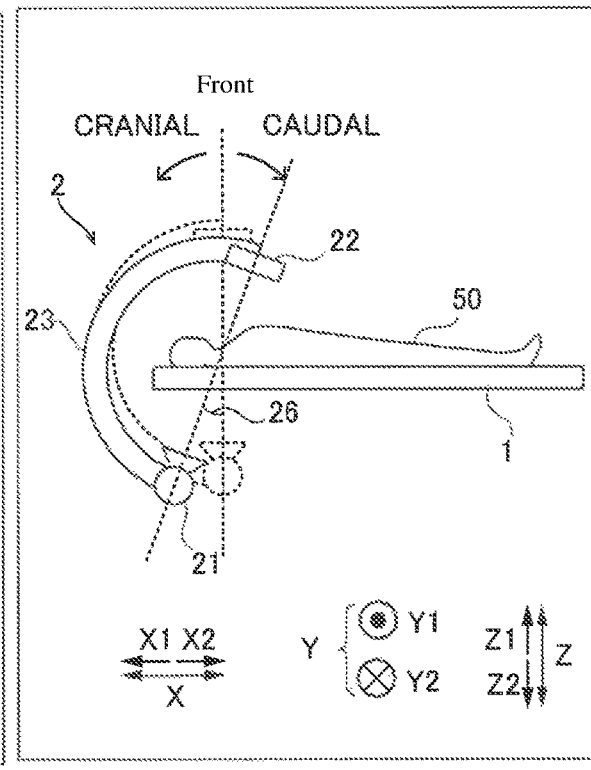
FIG. 8B is a diagram for explaining a circumferential rotation of an arm by a rotation mechanism when imaging at a CAUDAL position.

As shown in FIG. 8A, in a case where the target position 40 (see FIG. 1) is a CRANIAL position, the control unit 4 controls the rotation mechanism 61 so as to rotate the arm 23 in the X1-direction from the position shown by the dotted line to the position shown by the solid line. Further, as shown in FIG. 8B, in a case where the target position 40 is a CAUDAL position, unlike the case of the CRANIAL position, the control unit 4 controls the rotation mechanism 61 so as to rotate the arm 23 in the X2-direction from the position shown by the dotted line to the position shown by the solid line. Note that the position shown by the dotted line is a position where the arm 23 is to be arranged first and a combination of the front positions in FIG. 2A and FIG. 2B.

Figure 9:
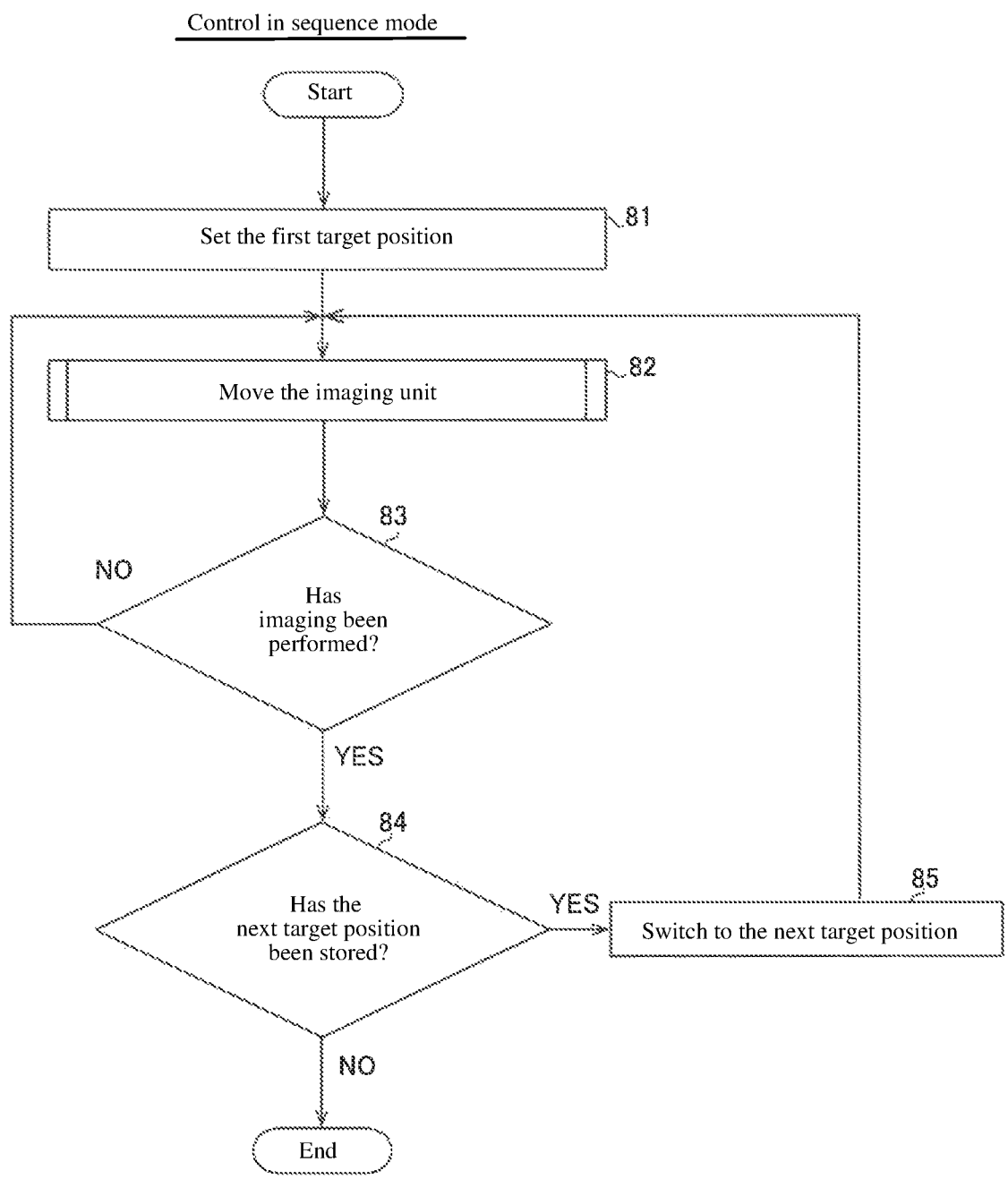
FIG. 9 is a flowchart showing an example of control by a control unit in a sequence mode.

The plurality of target positions 40 is set by the user in advance. For example, the control unit 4 makes the storage unit 3 store a plurality of target positions 40 and the order of imaging in an associated manner based on the operation input via the operation unit 5. The control unit 4 may perform control to replace the order of imaging the plurality of target positions 40, based on the operation input via the operation unit 5, Control In Sequence Mode The control of the control unit 4 of the X-ray fluoroscopic imaging apparatus 100 of this embodiment in a sequence mode will be described with reference to FIG. 9. In Step 81, the control unit 4 sets the first target position 40 among the plurality of target positions 40 stored in the storage unit 3 as a position toward which the imaging unit 2 is moved.

In Step 82, an operation for moving the imaging unit 2 toward the target position 40 is received via the first operation unit 51. Thus, the control unit 4 controls the rotation mechanism 61 and the moving mechanism 62 to move the imaging unit 2 toward the set target position 40. At this time, at the position where an input of the movement operation has not become available anymore, the control unit 4 terminates the control to move the imaging unit 2 regardless of whether or not the imaging unit 2 has reached the target position 40. Further, the control unit 4 receives an operation to move the imaging unit 2 in a direction different from a direction toward the target position 40 via the second operation unit 52. This controls the rotation mechanism 61 or the moving mechanism 62 to move the imaging unit 2 in a direction different from the direction toward the target position 40. As a result, the adjustment of the imaging position is performed.

In Step 83, the control unit 4 determines by the first determination unit 41 whether or not imaging has been performed. In a case where it is determined that imaging has been performed, the process proceeds to Step 84. In a case where it is determined that imaging has not been performed, the processing returns to Step 82.

In Step 84, the next Step changes depending on whether or not the next target position 40 has been stored in the storage unit 3. In a case where the next target position 40 has been stored in the storage unit 3, the process proceeds to Step 85 because the imaging of the subject 50 at the current target position 40 has been completed. In Step 85, the control unit 4 switches the next target position 40 as a position toward which the imaging unit 2 is moved. Then, the process returns to Step 82, and the processing from Step 82 to Step 85 is repeated.

In Step 84, in a case where the next target position 40 has not been stored in the storage unit 3, the control unit 4 terminates the sequence mode.

Figure 10:
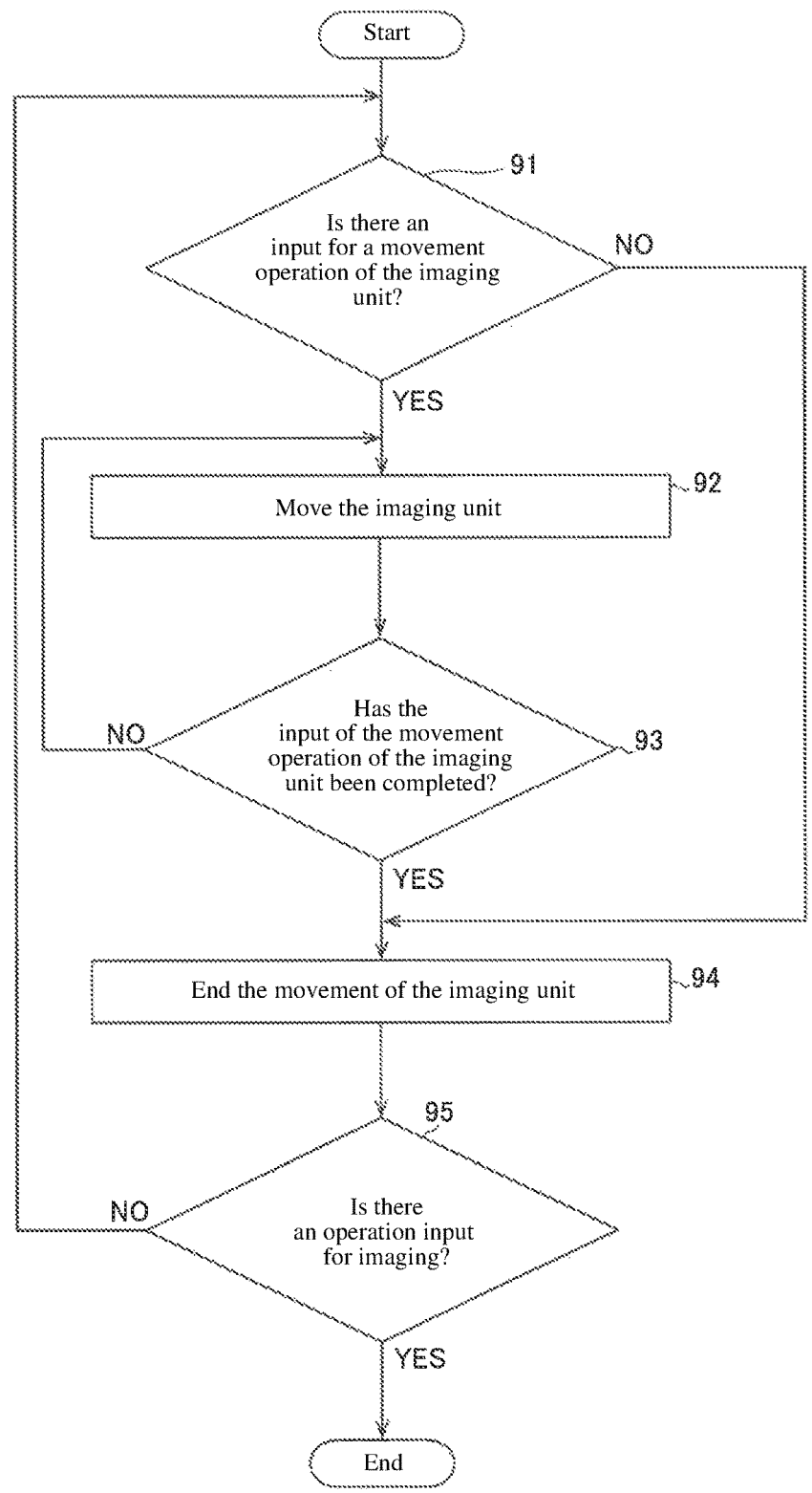
FIG. 10 is a flowchart showing an example of movement control of an imaging unit.

With reference to FIG. 10, the control to move the imaging unit 2 will be described in detail. In Step 91, the next Step changes depending on whether or not there is either the input of the movement operation of the operation unit 51 via the first imaging unit 2 or the input of the movement operation of the imaging unit 2 via the second operation unit 52. In a case where there is either the input of the movement operation of the imaging unit 2 via the first operation unit 51 or the input of the movement operation of the imaging unit 2 via the second operation unit 52, the process proceeds to Step 92. In Step 92, the control unit 4 controls the rotation mechanism 61 and the moving mechanism 62 to move the imaging unit 2. In a case where there is neither the input of the movement operation of the imaging unit 2 via the first operation unit 51 nor the input of the movement operation of the imaging unit 2 via the second operation unit 52, the process proceeds to Step 94. In Step 94, the control unit 4 terminates the control to move the imaging unit 2.

In Step 93, the next Step changes depending on whether or not the input of the movement operation of the imaging unit 2 via the first operation unit 51 and the input of the movement operation of the imaging unit 2 via the second operation unit 52 have been terminated. In a case where the input of the movement operation of the imaging unit 2 via the first operation unit 51 and the input of the movement operation of the imaging unit 2 via the second operation unit 52 have been terminated (in a case where there is neither of inputs), the process proceeds to Step 94. In Step 94, the control unit 4 terminates the control to move the imaging unit 2. In this case, regardless of whether or not the imaging unit 2 has reached the target position 40, the control unit 4 terminates the control to move the imaging unit 2. Then, the process proceeds to Step 95. Also, in a case where either the input of the movement operation of the imaging unit 2 via the first operation unit 51 or the input of the movement operation of the imaging unit 2 via the second operation unit 52 is being received, the process proceeds to Step 92. In Step 92, the control unit 4 performs control to move the imaging unit 2. Then, in Step 93, the control unit 4 controls the rotation mechanism 61 and the moving mechanism 62 to move the imaging unit 2 until the input of the movement operation via the first operation unit 51 or the second operation unit 52 of the movement operation via the second operation unit 52 has been completed. That is, the control unit 4 performs to control the rotation mechanism 61 and the moving mechanism 62 to move the imaging unit 2 while either the input of the movement operation via the first operation unit 51 or the input of the movement operation via the second operation unit 52 continues.

In Step 95, the proceeding step differs depending on whether or not there is an input operation to start imaging. In a case where there is an operation input to start imaging, the control unit 4 controls the rotation mechanism 61 and the moving mechanism 62 to terminate the control to move the imaging unit 2. In a case where there is no operation input to start imaging, the process returns to Step 91. The processing from Step 91 to Step 94 is repeated until there is an operation input to start imaging. Note that it is configured such that an operation input by the first operation unit 51 is not accepted at the time when the imaging unit 2 has reached the target position 40 during Step 94 from Step 91, but the operation via the second operation unit 52 is accepted. That is, it is configured to determine whether or not there is an input of the moving operation of the imaging unit 2 via the second operation unit 52 after reaching the target position.

Effects of This Embodiment

In this embodiment, the following effects can be obtained.

In the X-ray fluoroscopic imaging apparatus 100 of the present invention, as described above, the apparatus is provided with the bed 1, the imaging unit 2, the storage unit 3, the control unit 4, and the drive unit 6. The bed 1 is configured to place a subject 50 thereon. The imaging unit 2 includes the X-ray source 21 for irradiating the subject 50 with X-rays, the detector 22 for detecting X-rays emitted from the X-ray source 21, the detector being arranged to face the X-ray source, and the arm 23 for connecting the X-ray source 21 and the detector 22. The storage unit 3 stores a plurality of target positions 40 as targets toward which the imaging unit 2 is moved and the order of moving the imaging unit 2 toward the plurality of target positions 40 in an associated manner. The control unit 4 sequentially selects the plurality of target positions 40 in order. The drive unit 6 moves the imaging unit 2 toward the target position 40 switched by the control unit 4. The control unit 4 includes a first determination unit 41 for determining whether or not X-ray imaging has been performed. The control unit 4 is configured to perform control to switch the target position to the next target position when it is determined by the first determination unit 41 that X-ray imaging has been performed.

With this, in a case where it is determined by the first determination unit 41 that X-ray imaging has been performed, the control unit 4 completes imaging regardless of the position of the imaging unit 2 after moving when the control to switch the target position to the next target position has been completed. With this, since the control unit 4 performs control to switch the target position 40, it is possible to switch the target position 40 even in a case where imaging has been performed at a position other than the target position 40. Consequently, in a case where imaging has been performed at any imaging position, it is possible to switch the target position to the next target position 40 without selecting the next target position 40.

Further, in the above-described embodiment, the following further effects can be obtained by the following configuration.

That is, this embodiment is further provided with the position information acquisition unit 7 for acquiring the current information on the imaging unit 2 as described above. The control unit 4 includes the second determination unit 42 for determining whether or not the current position information of the imaging unit 2 acquired by the position information acquisition unit 7 matches the currently selected target position 40. When it is determined by the first determination unit 41 that X-ray imaging has been performed, the control unit 4 is configured to perform control to switch the target position to the next target position even when it is determined by the second determination unit 42 that the current position information of the imaging unit 2 does not match the currently selected target position 40, in addition to the case where it is determined by the second determination unit 42 that the current position information of the imaging unit 2 matches the currently selected target position 40. As a result, in a case where it is determined by the first determination unit 41 that X-ray imaging has been performed, the control unit 4 is configured to perform the control to switch the target position to the next target position even in a case where it is determined by the second determination unit 42 that the current position information of the imaging unit 2 does not match the currently selected target position 40, in addition to the case where it is determined by the second determination unit 42 that the current position information of the imaging unit 2 matches the currently selected target position 40. With this configuration, even in a case where imaging has been performed at a position different from the target position 40, the control unit 4 can switch the target position 40. As a result, it is possible to perform a series of imaging of the subject 50 while arbitrarily selecting the imaging position without performing an operation for switching the target position 40.

Further, in this embodiment, as described above, it is further provided with the operation unit 5 for receiving an operation for moving the imaging unit 2 toward the target position 40 and an operation for moving the imaging unit 2 in a direction different from a direction toward the target position 40. The control unit 4 performs control to move the imaging unit 2 toward the target position 40 stored in the storage unit 3 when the operation for moving the imaging unit 2 toward the target position 40 is received. Further, the control unit 4 performs control to move the imaging unit 2 in a direction different from a direction toward the target position 40 when the operation for moving the imaging unit 2 in a direction different from a direction toward the target position 40 is received. In a case where it is determined by the first determination unit 41 that X-ray imaging has been performed, the control unit 4 is configured to perform the control to sequentially switch the plurality of target positions 40 after completing the imaging. This allows the user to move the imaging unit 2 along the path toward the target position 40 and move the imaging unit 2 to a position deviating from the path toward the target position 40. Further, the control unit 4 is configured to perform control to sequentially switch the plurality of target positions 40 after completing the imaging even if the imaging unit 2 after moving has not yet reached the target position 40. Therefore, the control unit 4 can switch the target position 40 even in a case where the user has performed imaging at a position deviating from the path toward the target position 40 in addition to the case where the user has performed imaging on the path toward the target position 40. As a result, a series of imaging can be performed while adjusting the position at which the user performs imaging in accordance with the subject 50.

First Modification of this Embodiment

With reference to FIG. 1 to FIG. 8, FIG. 10, and FIG. 11, a first modification of this embodiment will be described. Note that the same components as those of the above-described embodiment are allotted by the same reference numerals, and the descriptions thereof will be omitted.

The first modification differs from the first embodiment as follows. In a case where the difference between the position of the imaging unit 2 at the end of imaging and the target position 40 toward which the imaging unit 2 is moved to perform imaging is within a preset range, the control unit 4 controls as follows. That is, even in a case where the imaging unit 2 after moving has not yet reached the target position 40, which is a case where it is determined by the second determination unit 42 that the current position of the imaging unit 2 does not match the target position 40, the control unit 4 performs control to sequentially switch the plurality of target positions 40 after completing the imaging. Further, in a case where the difference between the position of the imaging unit after completing the imaging and the target position 40 toward which the imaging unit 2 is moved to perform imaging is outside a preset range, the control unit 4 performs control not to switch the target position 40. The first modification is designed to prevent the target position from being switched due to the imaging unintended by the user, for example, when the same part has been imaged by mistake.

Figure 11:
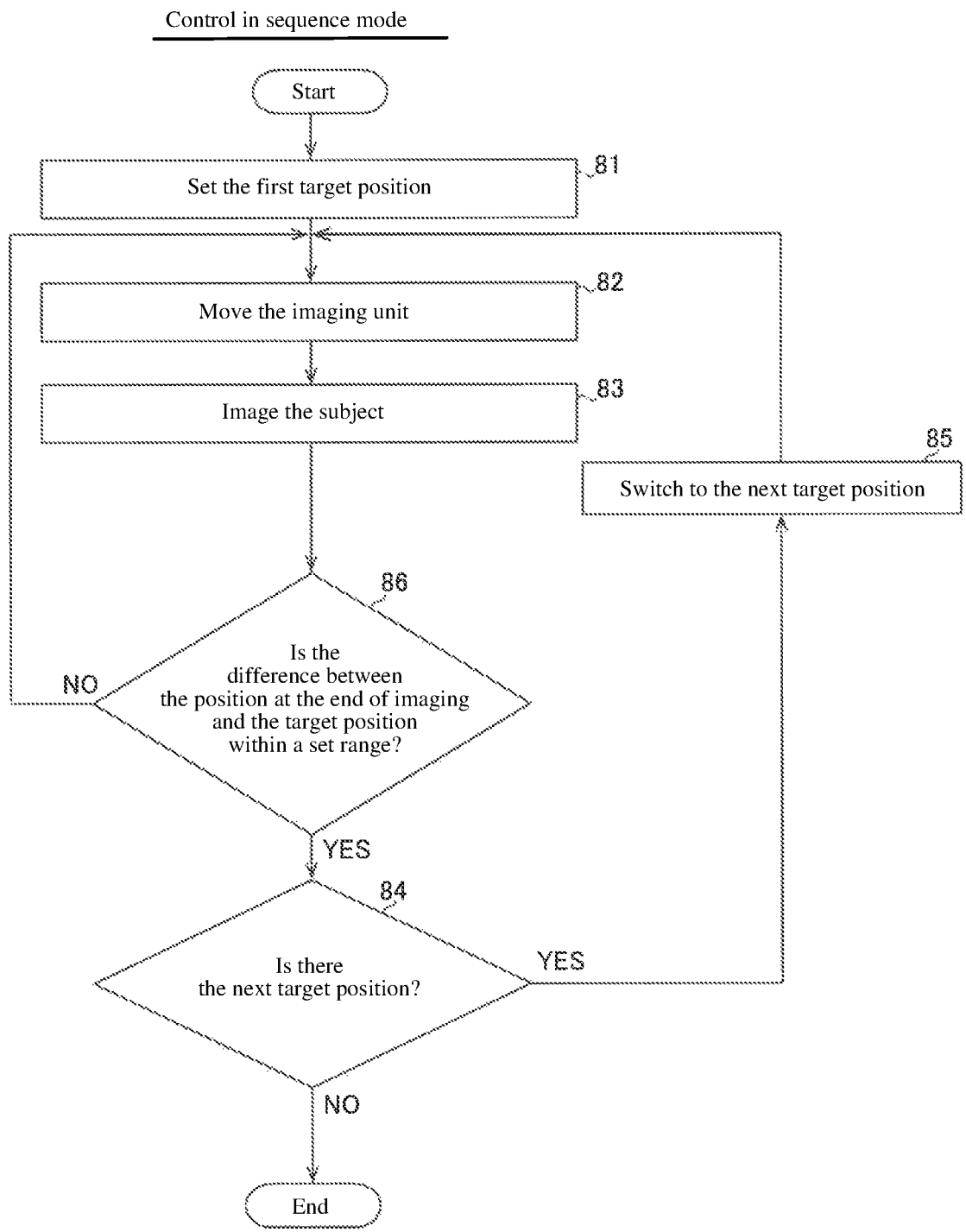
FIG. 11 is a flowchart showing an example of control by a control unit in a sequence mode according to a first modification.

As shown in FIG. 11, in the first modification, the range of the difference between the position of the imaging unit 2 at the end of imaging, which is a condition for switching the target position 40, and the target position 40 toward which the imaging unit 2 is moved to perform imaging is set. The range of the difference between the position of the imaging unit 2 at the end of imaging, which is a condition for switching the target position 40, and the target position 40 toward which the imaging unit 2 is moved to perform imaging is stored in the storage unit 3. The difference between the position of the imaging unit 2 at the end of imaging and the target position 40 toward which the imaging unit 2 is moved to perform imaging is a difference between the first rotation angles 25 (see FIG. 7A and FIG. 7B) and between the second rotation angles 26 (see FIG. 8A and FIG. 8B). The set range is the allowable range of the error between the first rotation angle 25 set to the current first rotation angle 40 and the first rotation angle at the position where the imaging was performed and the allowable range of the error between the second rotation angle 26 and the second rotation angle 26 at the position where the imaging was performed. The allowable range of the error is set, for example, within ±5 degrees or less. That is. in a case where the target position 40 is in the LAO40 position and the error is set to ±5 degrees, when the imaging position is positioned within a range from the LAO35 degrees to the LAO45 degrees, the control unit 4 performs control to switch the target position 40.

In a case where the difference between the position of the imaging unit 2 at the end of imaging and the target position 40 toward which the imaging unit 2 is moved to perform imaging is outside the preset range, the control unit 4 terminates the sequence mode. The control unit 4 does not switch the target position 40 even if an operation input for imaging via the third operation unit 53 is performed. Note that, in this case, the control unit 4 starts the sequence mode from the received target position 40 by receiving the selection of the new target position 40. The selection of the new target position 40 is performed by selecting one of the plurality of target positions 40 displayed on the display unit 8. At this time, the next target position 40 of the current target position 40 may be selected, and another target position 40 may be selected.

With reference to FIG. 11, the control of the control unit 4 in the sequence mode of the first modification will be described. First, the control from Step 81 to Step 85 is the same as that of this embodiment. Further, the movement of the imaging unit 2 in Step 82 is the same control as in FIG. 9. Unlike the above-described embodiment, in this first modification, Step 86 is performed after imaging is completed in Step 83 and before the process proceeds to Step 84. In Step 86, the following step changes depending on whether or not the difference between the position at the end of imaging and the target position 40 toward which the imaging unit 2 is moved is within the preset value.

In a case where the difference between the position of the imaging unit 2 at the end of imaging and the target position 40 toward which the imaging unit 2 is moved to perform imaging is within the preset range, the process proceeds to Step 84. In a case where the difference between the position at the end of imaging and the target position 40 toward which the imaging unit 2 is moved is outside the preset range, the process proceeds to Step 82.

The rest of the configurations of the first modification is the same as those of the above-described embodiment.

Effects of First Modified Example

In the first modification, as described above, the bed 1, the imaging unit 2, the storage unit 3, the control unit 4, and the drive unit 6 are provided. The bed 1 is configured to lay a subject 50 thereon. The imaging unit 2 includes the X-ray source 21 for irradiating the subject 50 with X-rays, the detector 22 for detecting X-rays emitted from the X-ray source 21, the detector 22 facing the X-ray source, and the arm 23 for connecting the X-ray source 21 and the detector 22. The storage unit 3 stores the plurality of target positions 40 serving as targets toward which the imaging unit 2 is moved and the order of moving the imaging unit 2 toward the target positions 40 in an associated manner. The control unit 4 sequentially selects the plurality of target positions 40 in order. The drive unit 6 moves the imaging unit 2 toward the target position 40 switched by the control unit 4. The control unit 4 includes the first determination unit 41 for determining whether or not X-ray imaging has been performed and is configured to perform control to switch the target position to the next target position when it is determined by the first determination unit 41 that X-ray imaging has been performed.

With this, when it is determined by the first determination unit 41 that X-ray imaging has been performed, the control unit 4 performs control to switch the target position to the next target position 40. With this configuration, the control unit 4 performs control to switch the target position 40 upon completion of imaging regardless of the position of the imaging unit 2 after moving. Therefore, the target position 40 can be switched even in a case where imaging has been performed at a position other than the target position 40. Consequently, in a case where imaging has been performed at any imaging position, it is possible to switch the target position to the next target position 40 without selecting the next target position 40.

Further, in the above-described first modification, the following further effects can be obtained by the following configuration.

In the first modification, as described above, in a case where it is determined ty the second determination unit 42 that the current position information of the imaging unit 2 does not match the currently selected target position 40, when the difference between the position of the imaging unit 2 at the end of imaging and the target position 40 toward which the imaging unit 2 is moved to perform imaging is within the preset range, the control unit 4 is configured to perform the following control. That is, the control unit 4 is configured to perform control to sequentially switch the plurality of target positions 40 after completion of the imaging even in a case where the imaging unit 2 after moving has not reached the target position 40. Further, the control unit 4 is configured to perform control not to switch the target position 40 in a case where the difference between the position of the imaging unit at the end of imaging and the target position 40 toward which the imaging unit 2 is moved to perform imaging is outside the preset range. Thus, for example, in a case where a plurality of imaging operations is performed at the same position, e.g., when imaging is performed again, by setting a value smaller than the difference between consecutive target positions 40 as the upper limit of the preset range, after switching to the next target position 40 in the first imaging, the second and subsequent imaging positions are not the switched target position 40 but the preceding target position 40. Therefore, the difference between the position of the imaging unit 2 at the end of the imaging and the target position 40 toward which the imaging unit 2 is moved to perform imaging is the difference between the consecutive target positions 40. Then, the difference between the position of the imaging unit 2 at the end of imaging and the target position 40 toward which the imaging unit 2 is moved to perform imaging becomes larger than the preset range. Therefore, the control unit 4 performs control not to switch the target position 40. As a result, it is possible to suppress the target position 40 from being sequentially switched every time imaging is performed at the same position.

Further, in the first modification, as described above, the arm 23 of the imaging unit 2 has an arc-shaped shape. The difference between the position of the imaging unit 2 at the end of imaging and the target position 40 toward which the imaging unit 2 is moved to perform imaging is the difference between the first rotation angles 25 at which the arm 23 of the imaging unit 2 rotates about a line extending in the longitudinal direction of the bed 1 connecting the head and the foot of the subject 50, and the difference between the second rotation angles 26 at which the arm 23 of the imaging unit 2 rotates in the circumferential direction of the arm 23 of the imaging unit 2. Here, in a case where the difference between at least either the first rotation angles 25 or the second rotation angles 26 is increased, there is a possibility that the position of the imaging unit 2 may largely deviate from the target position 40. Therefore, in a case where the difference between the first rotation angles 25 and the second rotation angles 26 between the second rotation angle and the target position 40 toward which the imaging unit 2 is moved to perform imaging is outside the range, the control unit 4 performs control not to switch the target position 40. With this, it is possible to suppress the target position 40 from being switched when imaging has been performed at a position largely deviating from the target position 40.

Further, in the first modification, as described above, in a case where the difference between the position of the imaging unit 2 at the end of imaging and the target position 40 toward which the imaging unit 2 is moved is outside the preset range and the control not to switch the target position 40 is performed, the control unit 4 is configured to perform control to switch the plurality of target positions 40 upon receipt of the operation input for performing control to switch to the target position 40. With this, in a case where the control unit 4 performs control not to switch the target position 40, the user can switch the target position 40 by performing the control to switch the target position to any target position 40. Consequently, the imaging can be started at any target position 40.

The other effects of the first modification are the same as those of the above-described embodiment.

Second Modification of This Embodiment

A second modification will be described with reference to FIG. 1 to FIG. 10 and FIG. 12. The same configuration as the above-described embodiment will be omitted using the same reference numerals.

Unlike the above-described embodiment, the second modification 3 is configured such that the storage unit 3 collectively stores target positions 40 of a plurality of sites. Note that the rest of the configurations of the second modification is the same as those of the above-described embodiment. Therefore, the same reference numerals are allotted, and the descriptions thereof will be omitted. The plurality of imaging positions is, for example, a combination of a blood vessel of a heart and a blood vessel of a lower limb.

Figure 12:
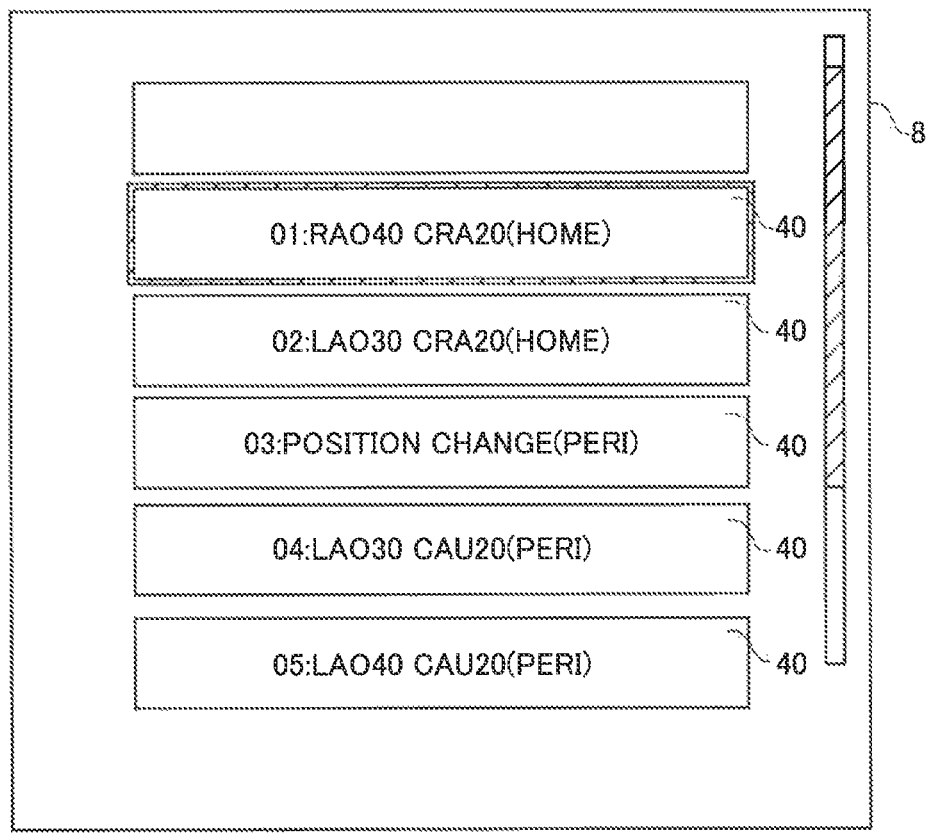
FIG. 12 is a diagram showing an example of target positions displayed on a display unit according to a second modification.

As shown in FIG. 12, the setting of the target positions 40 is performed for each site. For example, in a case where imaging is performed twice at each side, a target position 40 relating to the imaging of the first side as the first target position 40 and the second target position 40 is set. Further, a target position 40 relating to imaging of the second part as the third target position 40 and the fourth target position 40 is set. These are stored together in the storage unit 3.

The following description will be directed to the case in which the sites to be imaged are a blood vessel of a heart and a blood vessel of a lower limb. In this case, since the position of the blood vessel of the heart and the position of the blood vessel of the lower limb are separated from each other, it is necessary to change the relative position of the imaging unit 2 with respect to the bed 1 after imaging the position of the blood vessel of the heart. For example, after imaging the blood vessel of the heart at a HOME position, the control unit 4 controls the moving mechanism 62 to move the imaging unit 2 to a PERI position in order to image the blood vessel of the lower limb. Therefore, the setting of the target position 40 is set so as to include the moving of the relative position toward which the arm 23 is moved to perform imaging from the HOME position to the PERI position. For example, the target position 40 is set for the first and second imaging of the blood vessel of the heart, the relative position of the imaging unit 2 after moving to the bed 1 is set for the third imaging, and the relative position 40 for the imaging unit 2 after changing to the bed 1 is for the fourth imaging, and the relative position 40 of the imaging unit 2 after changing to the bed 1 is set for the fourth and fifth imaging. In FIG. 12, "POSITIONING CHANGE" indicates the change of the relative position of arm 23 with respect to the bed 1. Also, "PERI" after "POSITIONING CHANGE" indicates that the relative position after changing denotes the PERI position. The rest of the configurations of the second modification is the same as those of the above-described embodiment.

Effects of Second Modification

In the second modification, as described above, the bed 1, the imaging unit 2, the storage unit 3, the control unit 4, and the drive unit 6 are provided. The bed 1 is configured to lay a subject 50 thereon. The imaging unit 2 includes the X-ray source 21 for irradiating the subject 50 with X-rays, the detector 22 arranged to face the X-ray source 21 for the purpose of detecting the X-rays emitted from the X-ray source 21, and the arm 23 for connecting the X-ray source 21 and the detector 22. The storage unit 3 stores a plurality of target positions 40 serving as targets toward which the imaging unit 2 is moved to perform imaging and the order of moving the imaging unit 2 toward the plurality of target positions 40. The control unit 4 sequentially selects the plurality of target positions 40 in order. The drive unit 6 moves the imaging unit 2 toward the target position 40 switched by the control unit 4. The control unit 4 includes the first determination unit 41 for determining whether or not X-ray imaging has been performed. When it is determined by the first determination unit 41 that X-ray imaging has been performed, the control unit is configured to perform control to switch the target position to the next target position 40.

Thus, in a case where it is determined by the first determination unit 41 that X-ray imaging has been performed, the control unit 4 performs control to switch the target position to the next target position 40. Thus, the control unit 4 performs control to switch the target position 40 when the imaging has been completed regardless of the position of the imaging unit 2 after moving. Therefore, the target position 40 can be switched even in a case where imaging has been performed at a position other than the target position 40. Consequently, in a case where imaging has been performed at an arbitrary imaging position, it is possible to switch to the target position to the next target position 40 without selecting the next target position 40.

Further, in the above-described second modification, the following further effects can be obtained.

In the second modification, it is configured such that the target positions 40 of a plurality of sites are collectively stored in the storage unit 3. As a result, since the target positions 40 of the plurality of sites are configured to be collectively stored in the storage unit 3, there is no need to set the target position 40 for each target site. Therefore, it is possible to reduce the burden on the user who sets the target position 40.

The other effects of the second modification are the same as those of the above-described embodiment.

Modified Embodiments

It should be understood that the embodiments disclosed here are examples in all respects and are not restrictive. The scope of the present invention is shown by claims rather than the descriptions of the embodiments described above, and includes all changes (modifications) within the meaning of equivalent and the scope of claims.

For example, in the above-described embodiment and the above-described first modification, an example is shown in which the arm 23 is of a single-plane type, but the present invention is not limited to thereto. For example, it may be of a biplane type in which two arms 23 are provided. In this case, the target positions of each arm may be displayed side by side on the display unit. Further, the storage unit may collectively store the movements of each arm.

Further, in the above-described embodiment, first modification, and second modification, an example is shown in which the operation units 5 for receiving the operation for moving the imaging unit 2 toward the target position and the operation for moving the imaging unit 2 in a direction different from a direction toward the target position are different from each other, but the present invention is not limited thereto. For example, one operation unit may be configured to accept both the operations.

In the above-described embodiment, first modification, and second modification, an example is shown in which the display unit 8 is a touch panel for accepting an operation input, but the present invention is not limited thereto. For example, the display unit may be a display panel that does not accept the operation input.

In the above-described embodiment, first modification, and second modification, the operation unit 5 and the display unit 8 are provided on the side of the bed 1, but the present invention is not limited thereto. For example, the operation unit and the display unit may each be provided away from the bed.

Further, in the above-described embodiment, first modification, and second modification, an example is shown in which the difference between the position of the imaging unit 2 at the end of imaging and the target position 40 toward which the imaging unit 2 is moved to perform imaging is a difference between the first rotation angles 25 and the difference between the second rotation angles, but the present invention is not limited thereto. For example, the difference between the position of the imaging unit at the end of imaging and the target position toward which the imaging unit is moved to perform imaging may be the difference of the position coordinates showing the relative position between the imaging unit and the position coordinate.

Further, in the above-described first modification, an example is shown in which the selection of the new target position 40 is accepted via the display unit 8, but the present invention is not limited thereto. For example, the target position displayed on the display unit may be selected by operating the operation unit.

Further, in the second modification, an example is shown in which the relative position of the imaging unit 2 with respect to the bed 1 is changed because the plurality of sites is separated from each other, but the present invention is not limited thereto. For example, in a case where a plurality of sites, such as, e.g., a blood vessel of a heart and a blood vessel of a lung, is closely positioned, the change of the relative position may not be included in the target position because there is no need to change the relative position.

Although the second modification has been described as a modification of the above-described embodiment, the second modification may be provided with the configuration of the first modification.

Aspects

It will be understood by those skilled in the art that the above-described exemplary embodiments are concrete examples of the following aspects.

(Item 1)

An X-ray fluoroscopic imaging apparatus comprising:
a bed configured to place a subject thereon;
an imaging unit including an X-ray source for irradiating the subject with X-rays, a detector for detecting X-rays emitted from the X-ray source, the detector facing the X-ray source, and an arm for connecting the X-ray source and the detector;
a storage unit configured to store a plurality of target positions serving as targets toward which the imaging unit is moved and an order of moving the imaging unit to the plurality of target positions in an associated manner;
a control unit configured to sequentially switch the plurality of target positions according to the order; and
a drive unit configured to move the imaging unit toward a target position switched by the control unit,
wherein the control unit includes a first determination unit configured to determine whether or not X-ray imaging has been performed, and
wherein when it is determined by the first determination unit that X-ray imaging has been performed, the control unit is configured to perform control to switch the target position to a next target position.

(Item 2)

The X-ray fluoroscopic imaging apparatus as recited in the above-described Item 1, further comprising:
a position information acquisition unit configured to acquire current information on the imaging unit,
wherein the control unit further includes a second determination unit for determining whether or not the current position information on the imaging unit acquired by the position information acquisition unit matches a currently selected target position, and wherein when it is determined by the first determination unit that X-ray imaging has been performed, even in a case where it is determined by the second determination that the current position information on the imaging unit does not match the currently selected target position, in addition to a case where it is determined by the second determination unit that the current position information on the imaging unit matches the currently selected target position, the control unit performs control to switch the target position to the next target position.

(Item 3)

The X-ray fluoroscopic imaging apparatus as recited in the above-described Item 1 or 2, further comprising:

an operation unit configured to receive an operation for moving the imaging unit toward the target position and an operation for moving the imaging unit in a direction different from a direction toward the target position, wherein the control unit performs control to move the imaging unit toward the target position stored in the storage unit when an operation for moving the imaging unit toward the target position is received, control to move the imaging unit in a direction different from a direction toward the target position when an operation for moving the imaging unit in the direction different from the direction toward the target position, and a control to sequentially switch the plurality of target positions after completion of the imaging in a case where it is determined by the first determination unit that the X-ray imaging has been performed.

(Item 4)

The X-ray fluoroscopic imaging apparatus as recited in the above-described Item 2, wherein in a case where it is determined by the second determination unit that the current position information on the imaging unit does not match the currently selected target position, the control unit is configured to perform control to sequentially switch the plurality of target positions after completion of imaging even when the imaging unit after moving has not yet reached the target position in a case where a difference between the position of the imaging unit at an end of imaging and the target position toward which the imaging unit is moved to perform imaging is within a preset range, and control not to switch the target position in a case where the difference between the position of the imaging unit after imaging and the target position toward which the imaging unit is moved to perform imaging is outside the preset range.

(Item 5)

The X-ray fluoroscopic imaging apparatus as recited in the above-described Item 4, wherein the arm of the imaging unit has an arc-shaped shape, and wherein the difference between the position of the imaging unit at the end of imaging and the target position toward which the imaging unit is moved to perform imaging is a difference between first rotation angles at which the arm of the imaging unit rotates about a line extending in a longitudinal direction of the bed connecting a head and a foot of the subject and a difference between second rotation angles at which the arm of the imaging unit rotates in a circumferential direction of the arm of the imaging unit.

(Item 6)

The X-ray fluoroscopic imaging apparatus as recited in the above-described Item 4 or 5, wherein the control unit is configured to perform control to switch the plurality of target positions upon receipt of an operation input for selecting the target position.

(Item 7)

An X-ray fluoroscopic imaging method for an X-ray fluoroscopic imaging apparatus, the X-ray fluoroscopic imaging apparatus comprising an imaging unit for imaging a subject, and a plurality of target positions serving as targets toward which the imaging unit is performed and an order of moving the imaging unit toward the plurality of target positions being stored in an associated manner, the X-ray fluoroscopic imaging method comprising the steps of:

determining whether or not X-ray imaging has been performed by the imaging unit; and switching the target position to a next target position when it is determined that X-ray imaging has been performed.

The invention claimed is:

1. An X-ray fluoroscopic imaging apparatus comprising:

a bed configured to place a subject thereon;

an imaging unit including an X-ray source for irradiating the subject with X-rays, a detector for detecting X-rays emitted from the X-ray source, the detector facing the X-ray source, and an arm for connecting the X-ray source and the detector;

a storage unit configured to store a plurality of target positions serving as targets toward which the imaging unit is moved and an order of moving the imaging unit to the plurality of target positions in an associated manner;

a control unit configured to switch the plurality of target positions according to the order; and a drive unit configured to move the imaging unit toward a target position switched by the control unit; and an imaging operation unit configured to instruct the control unit to emit X-rays from the X-ray source when operated, wherein the plurality of target positions includes a first target position and a second target position that is a next target position after the first target position, wherein the control unit is configured to determine whether or not the imaging operation unit has been operated, wherein the control unit is configured to determine whether a difference between a position of the imaging unit at the time when the X-ray source emits the X-rays by operating the imaging operating unit and the first target position is within a preset range, wherein the control unit is configured to control to switch the target position from the first target position to the second target position in response to determining that the imaging operation unit has been operated, in a case where the difference between the position of the imaging unit at the time when the X-ray source emits the X-rays by operating the imaging operating unit and the first target position is within the preset range, and wherein the control unit is configured to control to maintain the target position at the first target position, in a case where the difference between the position of the imaging unit at the time when the X-ray source emits X-rays by operating the imaging unit and the first target position is not within the preset range, even in a case where the control unit determines that the imaging operation unit has been operated.

2. The X-ray fluoroscopic imaging apparatus as recited in claim 1, further comprising:
   a position information acquisition unit configured to acquire current position information on the imaging unit,
   wherein the control unit includes a first determination unit configured to determine whether or not the imaging operation unit has been operated,
   wherein the control unit further includes a second determination unit for determining whether or not the current position information on the imaging unit acquired by the position information acquisition unit matches a currently selected target position, and
   wherein when it is determined by the first determination unit that X-ray imaging has been performed, even in a case where it is determined by the second determination unit that the current position information on the imaging unit does not match the currently selected target position, in addition to a case where it is determined by the second determination unit that the current position information on the imaging unit matches the currently selected target position, the control unit performs control to switch the target position to the next target position.

3. The X-ray fluoroscopic imaging apparatus as recited in claim 1, further comprising:
   an operation unit configured to receive an operation for moving the imaging unit toward the target position and an operation for moving the imaging unit in a direction different from a direction toward the target position,
   wherein the control unit performs:
   control to move the imaging unit toward the target position stored in the storage unit when an operation for moving the imaging unit toward the target position is received,
   control to move the imaging unit in a direction different from a direction toward the target position when an operation for moving the imaging unit in the direction different from the direction toward the target position, and
   a control to sequentially switch the plurality of target positions after completion of the imaging in a case where it is determined by a first determination unit that X-ray imaging has been performed.

4. The X-ray fluoroscopic imaging apparatus as recited in claim 2,
   wherein in a case where it is determined by the second determination unit that the current position information on the imaging unit does not match the currently selected target position, the control unit is configured to perform:
   control to sequentially switch the plurality of target positions after completion of imaging even when the imaging unit after moving has not yet reached the target position in a case where a difference between a position of the imaging unit at an end of imaging and the target position toward which the imaging unit is moved to perform imaging is within a preset range, and
   control not to switch the target position in a case where the difference between the position of the imaging unit after imaging and the target position toward which the imaging unit is moved to perform imaging is outside the preset range.

5. The X-ray fluoroscopic imaging apparatus as recited in claim 4,
   wherein the arm of the imaging unit has an arc-shaped shape, and
   wherein the difference between the position of the imaging unit at the end of imaging and the target position toward which the imaging unit is moved to perform imaging is a difference between first rotation angles at which the arm of the imaging unit rotates about a line extending in a longitudinal direction of the bed connecting a head and a foot of the subject and a difference between second rotation angles at which the arm of the imaging unit rotates in a circumferential direction of the arm of the imaging unit.

6. The X-ray fluoroscopic imaging apparatus as recited in claim 1,
   wherein the control unit is configured to perform control to switch the plurality of target positions upon receipt of an operation input for selecting the target position.

7. An X-ray fluoroscopic imaging method for an X-ray fluoroscopic imaging apparatus, the X-ray fluoroscopic imaging apparatus comprising an imaging unit for imaging a subject, and a plurality of target positions serving as targets toward which the imaging unit performs the imaging and an order of moving the imaging unit toward the plurality of target positions being stored in an associated manner, the plurality of target positions includes a first target position and a second target position that is a next target position after the first target position,
   the X-ray fluoroscopic imaging method comprising the steps of:
   determining whether or not an imaging operation unit that is configured to instruct a control unit to emit X-rays from an X-ray source has been operated;
   determining whether a difference between a position of the imaging unit at the time when the X-ray source emits the X-rays and the first target position is within a preset range;
   switching the target position from the first target position to the second target position in response to determining that the imaging operation unit has been operated, in a case where the difference between the position of the imaging unit at the time when the X-ray source emits the X-rays and the first target position is within the preset range; and
   determining to maintain the target position at the first target position, in a case where the difference between the position of the imaging unit at the time when the X-ray source emits the X-rays and the first target position is not within the preset range, even in a case where it is determined the imaging operation has been operated.

* * * * *